United States Patent [19]
Bozzoni

[11] Patent Number: 5,994,124
[45] Date of Patent: Nov. 30, 1999

[54] RIBOZYME-SNRNA CHIMERIC MOLECULES HAVING A CATALYTIC ACTIVITY FOR NUCLEAR RNAS

[75] Inventor: Irene Bozzoni, Rome, Italy

[73] Assignee: Universita' Degli Studi Di Roma 'La Sapienza', Rome, Italy

[21] Appl. No.: 08/781,620

[22] Filed: Jan. 9, 1997

[30] Foreign Application Priority Data

Jan. 12, 1996 [IT] Italy ................................. RM96A0017

[51] Int. Cl.[6] .......................... C07H 21/02; C07H 21/04; A61K 48/00
[52] U.S. Cl. ........................ 435/320.1; 435/6; 435/91.31; 514/44; 536/23.1; 536/23.2; 536/24.1; 536/25.5
[58] Field of Search .......................... 435/6, 69.1, 172.1, 435/172.3, 320.1, 91.31, 440; 514/44; 536/23.1, 23.2, 24.5, 24.1

[56] References Cited

U.S. PATENT DOCUMENTS 5,695,938  12/1997  Rossi ............................................ 435/6

OTHER PUBLICATIONS

"Novel Approaches Towards the Nuclear Expression of Ribozyme and Antisense RNA Genes in Transgenic Mice" by Sharp et al., pp. 185–194, 1996.

"Synthesis of Chimeric RNAs between U6 small nuclear RNA and (–)sTRSV and Analysis of Their Cleavage Activities Against the Substrate RNA"by Tani et al.; Nucleic Acids Symposium Series vol. 27; 19–20, 1992.

"Functional Characterization of Ribozymes Expressed Using U1 and T7 Vectors for the Intracellular, Cleavage of ANF mRNA"by De Young et al.; Biochemistry 1994, 33 pp. 12127–12138.

"Self–Cleaving Motifs are Found in Close Proximity to the Sites Utilized for U16 snoRNA Processing"by Prislei et al.; Gene 163 (1995) pp. 221–226.

"Retroviral Vectors Designed for Targeted Expression of RNA Polymerase III–Driven Transcripts: A Comparative Study" by Ilves et al.; Gene. 171 (1996) pp. 203–208.

"Efficient Hammerhead Ribozyme–Mediated Cleavage of the Structured Hepatitis B Virus Encapsidation Signal In Vitro and in Cell Extracts, but not in Intact Cells" by Beck et al.; Nucleic Acids Research, 1995, vol. 23, No. 24, pp. 4954–4962.

Orkin et al "Report and Recommendations of the Panel to Assess the NIH Investment in Research on Gene Therapy", 1995.

Stull et al "Antigene Ribozyme and Aptamer Nucleic Acid Drugs: Progress and Prospects" Pharmaceutical Research vol. 12 No. 4; 465–483, 1995.

Burke, J., "Clearing The Way For Ribozymes" Nature Biotechnology vol. 15: 414, May 1997.

Tani, T., et al "Activity of chimeric RNAs of U6 snRNA and (–) STRSV in the Cleavage of a substrate RNA."NAR vol. 20 No. 12: 2991–2996, 1992.

Michienzi et al U1 Small Nuclear RNA chimeric ribozymes with substrate specifility for the Rev pre–mRNA of human immunodeficiency virus. PNAS vol. 93: 7219–7224, Jul. 1996.

*Primary Examiner*—George C. Elliott
*Assistant Examiner*—Sean McGarry
*Attorney, Agent, or Firm*—Baker & Botts, L.L.P.

[57] ABSTRACT

The invention is drawn to a chimeric ribozyme molecule that comprises a U1 snRNA component and a ribozyme component where the chimeric ribozyme targets an mRNA in the spliceosome in the nuclease of a cell.

13 Claims, 6 Drawing Sheets

RIBOZYME-SNRNA CHIMERIC MOLECULES HAVING A CATALYTIC ACTIVITY FOR NUCLEAR RNAS

The invention concerns ribozyme-snRNA chimeric molecules, having a ribozyme mediated catalytic activity towards specific target RNAs, and a snRNA component to efficiently vehicle the molecule to the target site. The molecules of the invention can be used either in the biomedical research field, or when a specific targeting of a ribozyme is desired, as for anti-viral therapies, in particular for the anti-HIV (Human immunodeficiency virus) intracellular immunization.

Ribozymes are RNA molecules having an endonucleolytic (catalytic) activity. Ribozymes exhibit such activity either in vitro or in vivo (1,2,3). Indeed, until now several examples have been reported in which ribozymes have been utilized as anti-HIV molecules in vitro (4,5,6).

U1 snRNAs (small nuclear RNAs) show a "stem and loop" tridimensional structure, wherein loops are numbered progressively starting from the 5' end of the molecule.

SnRNAs are involved with the processing of introns (splicing) starting from pre-mRNAs. U1 is involved during the first splicing steps.

One major problem related to the use in vivo of ribozymes therapy is that while in test tubes these molecules and their substrates can diffuse freely, in cells RNAs are sorted to specific cellular locations. Viral RNAs are also specifically compartmentalized in vivo, and this feature may reduce their availability for ribozyme interaction.

There is therefore the need for set up new strategies to specifically target ribozymes to the desired cell compartment.

The author of the instant invention has developed new chimeric molecules able to vehicle specifically in vivo ribozymes to the target RNA in the cell, such providing for selective and specific therapeutic agents. The molecules of the invention comprise a first ribozyme-derived component having a catalytic activity towards a target RNA and a second component acting as vector to specifically target the molecule itself to the desired cell compartment. According to a preferred embodiment of the invention, provided that the cell compartment is the cell nucleus, the second component acting as vector is a snRNA.

The author of the invention has used either *X. laevis* or human snRNAs and has shown a correct in vivo cell compartmentalisation of derived chimeric molecules, and a catalytic activity when the HIV pre-mRNA substrate was used.

Moreover the author has advantageously modified the nucleotide sequence of the vector component to optimize the binding thereof to the target RNA.

It is therefore an object of the invention to provide a chimeric molecule comprising:
  a vector component able to vehicle said molecule to a substrate target RNA; and covalently bound to said vector a ribozyme derived component having a catalytic activity towards said target RNA.

Preferably said vector component is derived from a snRNA, provided that said target substrate RNA is located into the nucleus, more preferably said snRNA is the U1 snRNA.

According to a preferred embodiment said snRNA is either from *X. laevis* or from mammalians, preferably humans.

According to a preferred embodiment, a portion of the nucleotide sequence of the U1 snRNA is substituted with the nucleotide sequence portion of a ribozyme having a catalytic activity towards a target substrate RNA, provided that said substitution does not impair substantially the capacity of said U1 snRNA to vehicle the molecule itself to said target substrate RNA. Preferably said nucleotide sequence portion of said U1 snRNA is the portion forming the stem-loop III structure of U1 snRNA.

According to another aspect of the invention the target substrate RNA is either an altered form of cellular RNA or a viral RNA. An "altered form of cellular RNA" is to be intended as a cellular RNA modified by mutations. Preferably said viral RNA is a HIV RNA, more preferably said viral RNA is the pre-mRNA REV of HIV.

According to another aspect of the invention the portion of the ribozyme sequence of said chimeric molecule is either identical or substantially homologous to the sequence of SEQ ID No. 1:

5'-AUGAGUCUCUGAUGAGUCCGUGAGGACGAAACUGCCUU-3'.

provided that said homology maintains its functional activity.

According to a preferred embodiment the snRNA component of the chimeric molecule is modified to increase its affinity for the target substrate RNA, preferably by means of nucleotide substitutions of the sequence recognizing the splicing site of said target substrate RNA.

According to a particular aspect of the invention the chimeric molecule is either identical or substantially homologous to the sequence of SEQ ID No. 2:

```
AUACUUACC UGGCAGGGGA GAUACCAUGA UCACGAAGGU GGUUUUCCCA GGGCGAGGCU

UAUCCAUUGC ACUCCGGAUG UGCUGACCCC UGCGAUGAGU CUCUGAUGAG UCCGUGAGGA

CGAAACUGCC UUCGACUGCA UAAUUUGUGG UAGUGGGGGA CUGCGUUCGC GCUUUCCCCU,
``` provided that said homology maintains the capacity of the vector component to vehicle the molecule itself to a target substrate RNA and of the ribozyme derived component to have a catalytic activity for said target substrate RNA.

It is a further object of the invention a nucleic acid coding one of any molecules of the invention. Preferably said nucleic acid has a sequence comprised in SEQ ID No.3, as follows:

```
AGGGCGACTT CTATGTAGAT GAGGCAGCGC AGAGGCTGCC TTGTTCGCCA CTTGCTGCTT 60

CACCACGAAG GAGTTCCCGT GCCCTGGGAG CGGGTTCAGG ACCGCTGATC GGAAGTGAGA 120
```

-continued

```
ATCCCAGCTG TGTGTCAGGG GTGGAAAGGG CTCGGGAGTG CGCGGGGCAA GTGACCGTGT180

GTGTAAAGAG TGAGGGTATG AGGCTGTGTC GGGGCAGAGG CCCAAGATCT CATACTTACC240

TGGCAGGGGA GATACCATGA TCACGAAGGT GGTTTTCCCA GGGCGAGGCT TATCCATTGC300

ACTCCGGATG TGCTGACCCC TGCGATGAGT CTCTGATGAG TCCGTGAGGA CGAAACTGCC360

TTCGACTGCA TAATTTGTGG TAGTGGGGGA CTGCGTTCGC GCTTTCCCCT GACTTTCTGG420

AGTTTCAAAA GTAGA,
``` or a complementary strand thereof.

According to a further aspect said nucleic acid is used for making vectors to be used for gene therapy of pathologies either derived from altered cellular RNAs or from viral RNAs. The method comprises retroviral subcloning steps and further infections or any related methods of nucleic acid delivery to the cells, according to technologies known to the experts in the field. Preferably said viral pathologies comprise HIV infection related pathologies.

It is a further object of the invention the chimeric molecule of the invention for use in therapy.

It is a further object of the invention a pharmaceutical composition comprising in an effective and acceptable dosage form a chimeric molecule according to the invention to be used for gene therapy of pathologies either derived from altered cellular RNAs or from viral RNAs. Preferably said chimeric molecule has a catalytic activity for a viral RNA, more preferably said viral RNA is a HIV RNA, most preferably is the HIV REV pre-mRNA.

The invention will be described for illustrating but not limiting purposes with reference to the following figures:

FIGS. 1a and b represent a scheme of construction and sequences of the U1-chimeric ribozymes. Panel a): schematic representation of the structure of the wild type and chimeric U1 snRNAs; the stem-loop III U1 snRNA sequence is substituted with the ribozyme hammerhead sequence (7). The sequences inserted (SEQ ID NO:19) are indicated below: bold nucleotides constitute the hammerhead catalytic core and the underlined nucleotides indicate the region of complementarity to the target RNA. The arrow indicates base substitutions in the inactive constructs. Panel b): sequences of canonical pre-mRNA 5' splice sites (SEQ ID NOS:20 and 21) are shown together with the complementary U1 snRNA sequences (high). Underlined nucleotides indicate the substitutions introduced in the U1 snRNA such as to have a perfect match with the 5' splice site of REV pre-mRNA (SEQ ID NO:4).

FIGS. 3a and b represent an in vitro analysis of chimeric molecules activity. Panel a): 0.15 μm of unlabelled chimeric molecules (U1-Rz, U1-Rz$_m$ and tRNA-Rz) were incubated for the indicated minutes with 0.05 μM of $^{32}$P-labelled REV substrate (S, 166 nucleotides long). The products of the reaction (5'—53 nucleotides long and 3'—113 nucleotides long) were analyzed on a 6% acrylamide-urea gel. Panel b): 0.4 μM of cold U1-Rz and 0.1 μM of $^{32}$P-labelled REV substrate were coincubated at three different temperatures (25° C., 30° C. and 37° C.) for the indicated minutes. The products of the reaction were analyzed on a 6% acrylamide-urea gel. Panel c): The expected reaction products: S, 166 nucleotides long; 5'—53 nucleotide long; and 3'—113 nucleotodies long.

FIG. 4 shows the cellular compartmentalisation of the U1-chimeric ribozymes. Plasmid DNAs coding for U1-Rz, U1-Rz-5' and U1h-Rz were injected into the nuclei of X. laevis oocytes and incubated overnight. Four nuclei (lanes N) and the corresponding cytoplasms (lanes C) were manually dissected and the RNA analyzed by Northern blot with a U1 snRNA specific probe. Four additional nuclei were utilized for immunoprecipitation with Sm antibodies, able to recognize U1 snRNA specifically associated proteins (Dr. Ian Mattaj, EMBL, Heidelberg, Germany), before RNA extraction (lanes Sm). The endogenous U1 snRNA and the U1-ribozymes (20 nucleotides longer) are indicated.

FIG. 5 shows the in vivo cleavage activity of chimeric molecules. 10 nl of a solution containing 1 ng of SP-REV plasmid and 3 ng of each one of the different U1 constructs (U1 w.t., lane 1; U1-Rz, lane 2; U1-Rz$_m$, lane 3; U1-Rz-5', lane 4 and U1-Rz-5'$_m$, lane 5) were injected into the nuclei of X. laevis oocytes and incubated overnight. As an internal control, in vitro transcribed $^{32}$P-labelled U6 snRNA was also coinjected. RNA from pools of same number of nuclei was extracted and analyzed by Northern blotting on 6% agarose-urea gel. The direct autoradiography of the polyacrylamide gel allows the visualization of the U6 RNA signal; while hybridizations with REV and U1 RNA probes allow to quantify the REV pre-mRNA and the expression of different ribozymes, respectively.

The target chosen for testing ribozyme activity is the REV pre-mRNA of the HIV virus (8,9,10). U1 snRNA was chosen as vector since it has nuclear localization and it is known to participate in the splicing reaction. The specificity of U1 snRNA interaction inside the spliceosome resides in the base pairing with the 5' splice junction of the substrate pre-mRNA. In REV pre-mRNA this sequence is suboptimal and reduces splicing efficiency. In order to increase the specificity of the U1-ribozyme for the REV pre-mRNA, mutations were introduced in the 5' splice site pairing region of U1 snRNA such as to match it with the suboptimal 5' junction of the REV precursor. The use of said vectors should confer these features to the ribozyme: i) stability, ii) nuclear localization and iii) increased substrate specificity for the REV precursor. U1 snRNA should vehicle the ribozyme on the REV pre-mRNA, increasing the relative concentration of ribozyme and substrate thus allowing efficient cleavage. In addition, the use of a REV-specific U1 snRNA should increase the specificity of the U1-ribozyme for the REV precursor with respect to all the other endogenous unmodified U1 RNA.

The author of the invention has tested the activity of these ribozymes either in vitro or in vivo by means of X. laevis oocytes, which represent an ideal in vivo system for the study of RNA compartmentalisation and accumulation. The author has found that the chimeric ribozymes are stable and correctly compartmentalise inside the nucleus where they display cleavage activity specific for the REV pre-snRNA. The author has also sinthesized human U1 snRNA derived chimeric molecules and shown that they correctly vehicle and exert their catalytic activity in HIV infected human cells. Said cells reveal a diminished viral replication, assayed by means of a decrease of HIV p24 protein levels in the culture medium.

EXAMPLE 1

Ribozyme Construction

The sequence of the hammerhead active and inactive core were derived from the studies of Uhlenbeck and Haseloff (2,11,12). The cleavage site of the REV sequence corresponds to the C (underlined) at position 5597 of the HIV genome (18) and is as follows:

```
5'-UCAAGGCAGUCAGACUCAUCA-3' (SEQ ID No.4).
```

The U1-chimeric ribozymes (U1-Rz) were obtained by inverse PCR on the XIU1-340 clone (14) containing the entire U1 RNA gene or on its T7 derivative which allows in vitro transcription under the T7 promoter. The oligonucleotides utilized are:

```
A: 5'-GGACTCATCA(G/C)AGACTCATCACGCAGGGGTCAGCACAACCGGA-3' (SEQ ID No.5);

B: 5'-GTGAGGACGAAACTGCCTTGACGACTGCATAATTTCTGGTAGT-3' (SEQ ID No. 6).
```

The degeneration of the A oligo allows the simultaneous construction of both the active and the inactive ribozymes.

The U1-Rz-5' was obtained by inverse PCR with U1 Rz and U1 Rz$_m$ by using the following oligos:

```
C: 5'-TGGGCAGGGGAGATACCATG-3' (SEQ ID No.7);

D: 5'-GTAAGTATGAGTTGAACAAG-3' (SEQ ID No.8).
```

The ribozyme for the tRNA was obtained by inverse PCR with a tRNApro (15) cloned in the Eco RI site of the Bluescript vector. Oligos were:

```
1: 5'-GGACTCATCAGAGACTCATGAGAATCATACCACTAGACCAT-3' (SEQ ID No. 9);

2: 5'-GTGAGGACGAAACTGCCTTTGGGTGCGAGAGGTCCCGGGTT-3' (SEQ ID No. 10).
```

EXAMPLE 2

Construction of REV Substrates

A 2510 nucleotide long fragment, covering the first coding exon (76 nt), the entire intron (2330 nucleotides) and 104 nt of the second coding exon of REV was generated by PCR amplification of the HIV clone BH10 (13).

The primers included the EcoRI and BamHI sites that allow the cloning in the corresponding sites of the pGEM4Z (Promega) vector to generate clone pGEM-REV. The BamHI digestion of this clone allows the in vitro transcription of the entire cloned sequences, while the AvaII digestion produces a template for the transcription of a 166 nucleotide long RNA that was utilized for the in vitro analysis of ribozyme activity. An EcoRI-BamHI digestion allows the cloning of REV sequences between the X. laevis L14 protein gene promoter and the SV40 polyadenylation site of the 166pTCAT vector. Said construct allows efficient expression of the REV pre-mRNA in a polyA+ RNA (16).

EXAMPLE 3

Ribozyme-U1 snRNA Construction

The 22 nucleotide sequence of the U1 snRNA stem-loop III (7) was substituted with the 42 nucleotide fragment comprising the ribozyme hammerhead catalytic core (12) and flanking sequences complementary to the target site region (at position 5598, according to 13). The stem-loop structure substitution was made since said structure i) does not participate in the correct compartmentalisation of the mature U1 snRNP particle (7,17); ii) is not essential for the U1 snRNA stability (18).

Figure 1A:
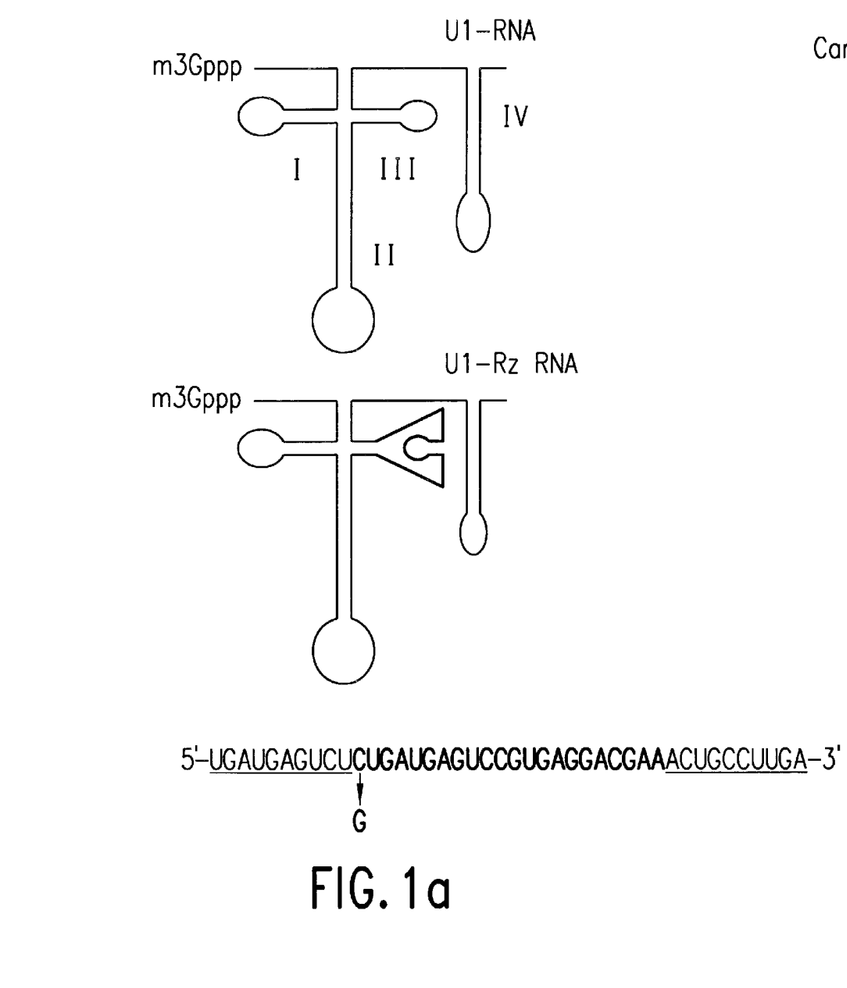
Figure 1B:
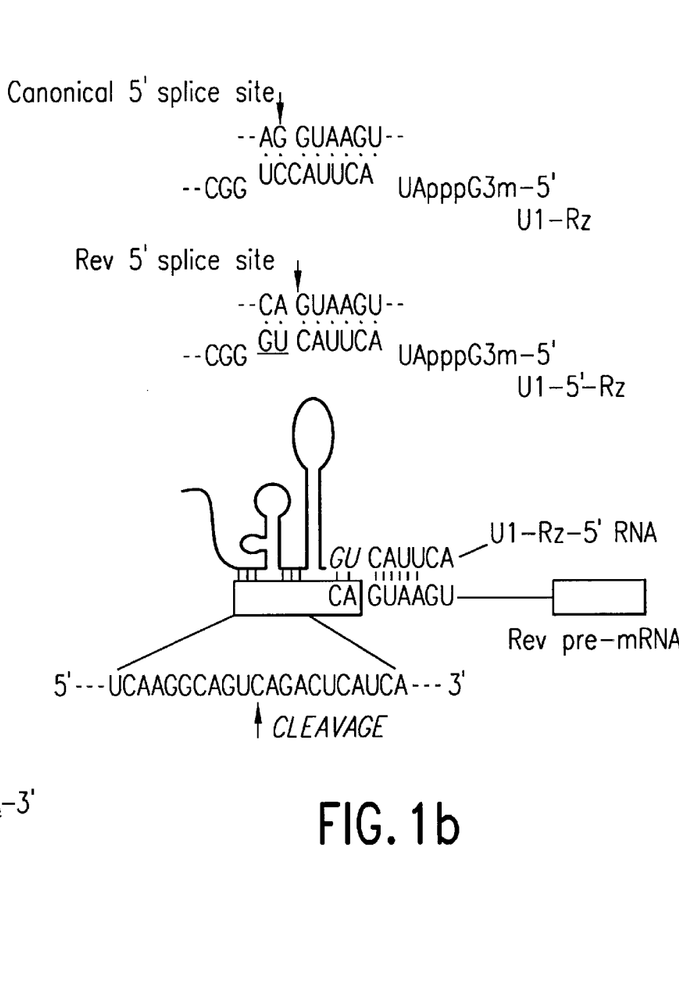

The target sequence is of 20 nucleotides of the first coding exon of pre-mRNA REV (see FIG. 1). A U1-Rz-5' construct was derived from U1-Rz, wherein the U1 snRNA 5'end (5'-GAU<u>ACUUACC</u>UGGC-3', SEQ ID No.11) was modified to 5'-GAU<u>ACUUACU</u>GGGC-3' (SEQ ID No.12). Said substitutions (bold) in the pairing region of the 5' end splice junction (underlined) produces a U1 snRNA having a perfect matching with the natural suboptimal 5' splice site of the REV pre-mRNA.

The same mutation was introduced both in the X. laevis U1 snRNA gene and in the T7 construct. As a control, the hammerhead catalytic core and the flanking sequences were cloned in a tRNA vector (15) just 5' of the anticodon loop (tRNA-Rz).

In order to control the ribozyme antisense effect, U1-Rz and U1-Rz-5' derived constructs were made by substituting the C in the hammerhead catalytic core (<u>C</u>UGAUGA) with G, thus abolishing the cleavage activity (12). Said constructs, named as U1-Rz$_m$ and U1-Rz$_m$-5' respectively, have an antisense effect but lack of catalytic activity.

Figure 2A:
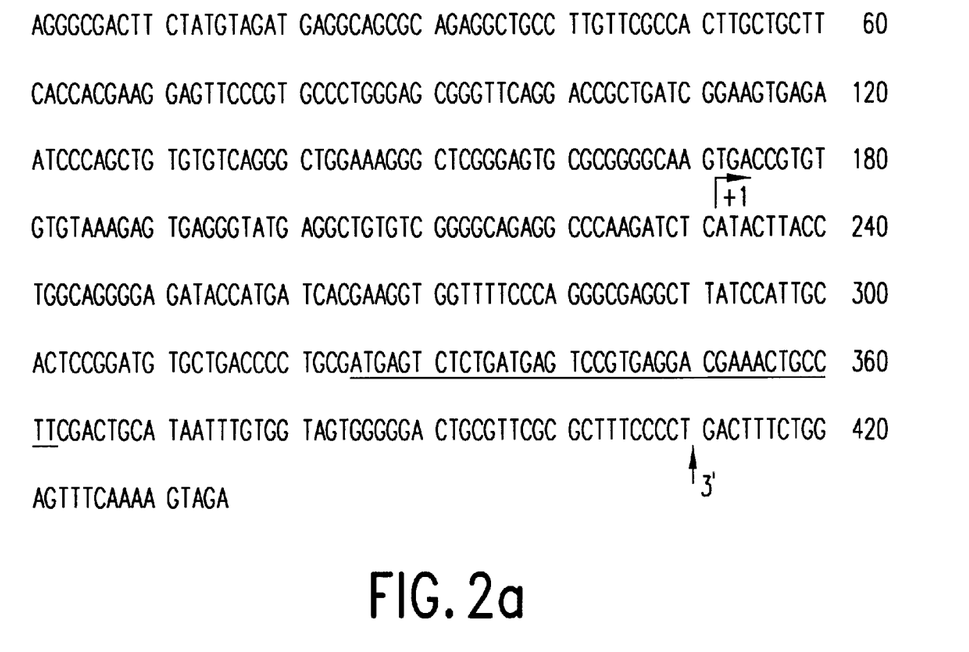
FIGS. 2a and b represent the nucleotide sequence of DNA coding the chimeric molecule U1h-Rz (SEQ ID NO:3; panel 2a) and modified at nucleotides 239–240 (U1-RZ-5's, SEQ ID NO:22; panel 2b) to optimize the binding to REV pre-mRNA. A bent arrow-+1 indicates the transcription start-cap site, an upward pointing arrow 3' indicates the 3' end of the transcript, and underlining indicates the ribozyme sequence. The first 230 nucleotides constitute the U1-RZ gene promoter.
Figure 2B:
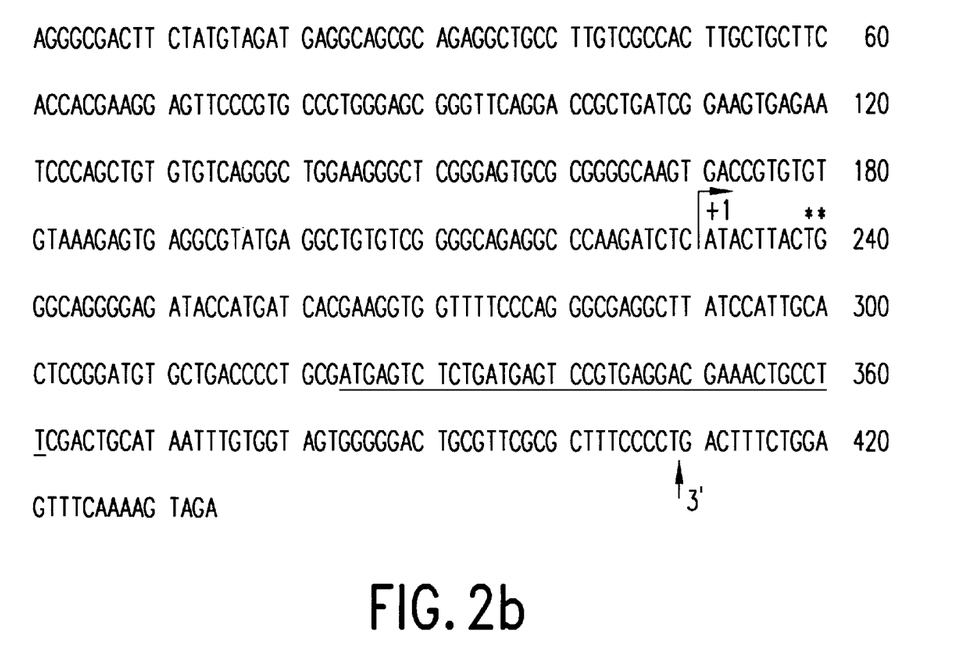

Analogous experiments were made to synthesize molecules with human snRNA, obtaining the U1h-Rz (FIG. 2a) and U1h-Rz-5'S (FIG. 2b) chimeric molecules, wherein the recognizing specifity towards the HIV REV pre-mRNA was increased by substituting of nucleotides no. 239–240.

Briefly the human U1 snRNA gene was obtained by PCR cloning from total genomic human DNA with the following primers:

E: 5'-CCGGATCCTAAGGACCAGCTTCTTTGGG-3' (SEQ ID No.13)

F: 5'-CCGGATCCTTAGCGTACAGTCTACTTTT-3' (SEQ ID No.14).

The cloned fragment comprises 400 bases upstream to the transcription start site and 40 bases downstream (+40) to the transcript 3'end (the sequence of FIG. 2 shows a more limited region, from −230 to +40).

In order to synthesize the ribozyme-U1h chimeric molecules, the following nucleotides were used:

G: 5'- GGACTCATCA(G/C)AGACTCATCGCAGGGGTCAGCACATCCGGA-3' (SEQ ID No.15)

H: 5'- GTGAGGACGAAACTGCCTTCGACTGCATAATTTGTGGTAGT-3' (SEQ ID No.16).

In order to synthesize the U1h-Rz-5' chimeric molecules, the following nucleotides were used:

I: 5'-TGGGCAGGGGAGATACCATG-3' (SEQ ID No.17)

L: 5'-GTAAGTATGAGATCTTGGGC-3' (SEQ ID No.18).

In all of said clones the hammerhead sequence has a 18 nucleotide sequence pairing with the substrate.

EXAMPLE 4

In Vitro Chimeric Ribozyme Activity

Ribozymes and $^{32}$P-labelled substrate RNAs were in vitro transcribed from the corresponding T7 constructs. Ribozyme and substrate (0.15 µM and 0.05 µM respectively, or 0.4 µM and 0.1 µM) in 50 mM Tris-HCl pH 7.5 were heated at 95° C. for 2 min and cooled 5 min in ice. 10 mM MgCl$_2$ was added and the reactions allowed to proceed at 37° C., or when specified at different temperature, for the indicated times. The RNA was analyzed on 6% polyacrylamide-7M urea gels.

Figure 3A:
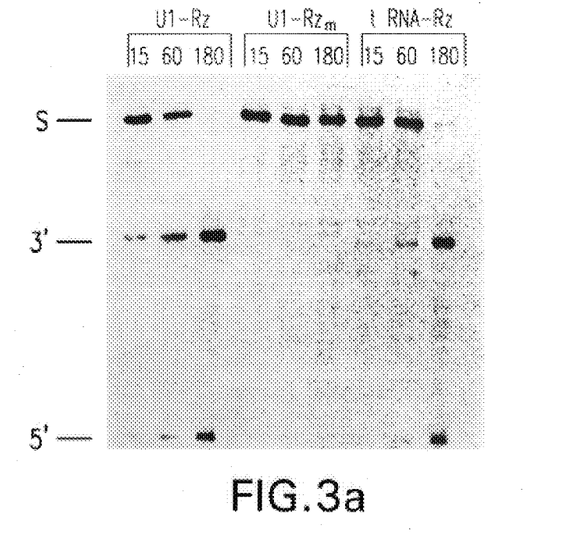

T7 transcripts of U1-Rz and U1-Rzm (186 nt) were coincubated with $^{32}$P labelled REV target site (band S, 166 nucleotides). FIG. 3a shows a time course of incubation of 0.15 µM of ribozyme and 0.05 µM of substrate at 37° C. in 10 mM MgCl$_2$ and 50 mM Tris-HCl pH 7.5. It appears that the U1-Rz converts the substrate (band S, 166 nucleotide long) very efficiently into the expected cleavage products (bands 5' and 3'), whereas in the same conditions no cleavage is produced by the mutant ribozyme (lanes U1-Rz$_m$). Interestingly, the tRNA-Rz works less efficiently than the U1-Rz as demonstrated by the reduced conversion of the substrate into truncated products (lane tRNA-Rz).

Figure 3B:
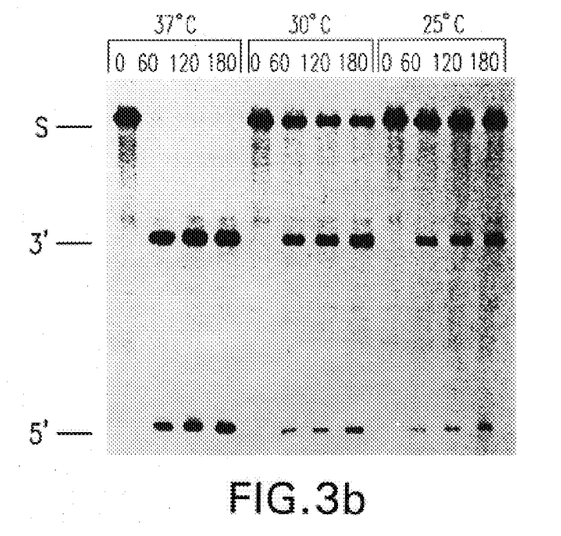
Figure 3C:
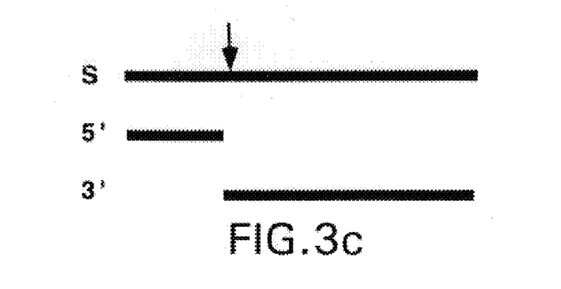

FIG. 3b shows the temperature-dependent activity of the U1-Rz, in an experiment with a 4:1 ribozyme:substrate molar ratio. It appears that at 25° C. the activity of the ribozyme is strongly reduced with respect to 37° C.

EXAMPLE 5

Expression and In Vivo Localization of U1-Rz Transcript

Figure 4:
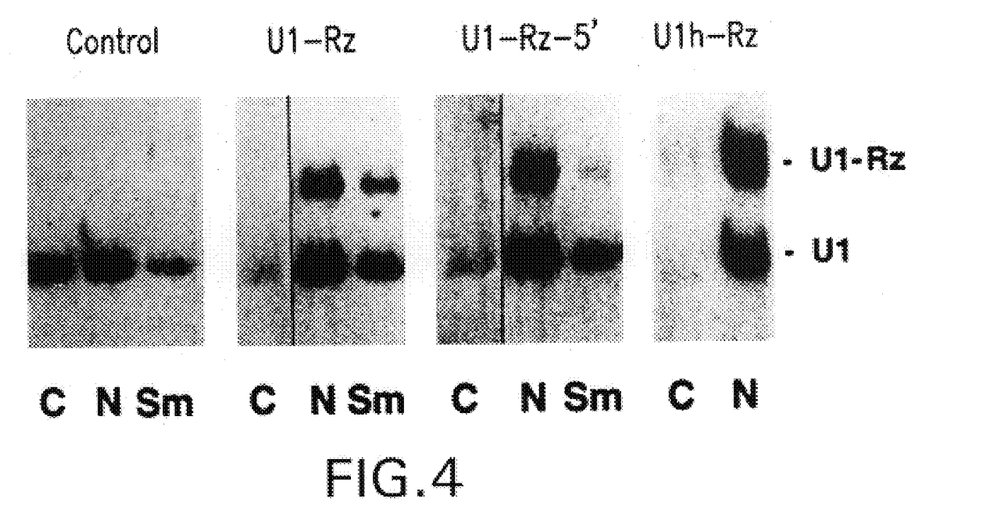

Plasmid DNAs, after purification on CsCl gradients, were dissolved in 80 mM NaCl, 10 mM Tris pH 7.0 at a concentration of 400 ng/µl and 10 nl were injected into the germinal vesicles of stage VI X. laevis oocytes according to Caffarelli et al. (19). After incubation the nuclei were manually separated from cytoplasms and RNA was extracted from the two different compartments. FIG. 4 shows a Northern analysis performed with control oocytes (lanes control) and with oocytes injected with the U1-Rz (lanes U1-Rz) and U1-Rz-5' (lanes U1-Rz-5') genes. Both of U1-chimeric ribozymes are efficiently expressed and stably accumulate inside the nucleus. High levels of expression and correct nuclear compartmentalisation are observed also for the human (lanes U1h-Rz) and mutant constructs (not shown).

An immunoprecipitation with Sm antibodies was utilized to test whether the U1-chimeric ribozymes are able to form U1 snRNP-like complexes. FIG. 4 shows that both U1-Rz and U1-Rz-5' are reactive to Sm antibodies. The non-quantitative immunoprecipitation may be due either to the altered particle conformation, or to the competition of the endogenous U1SnRNP which is in excess and do represent the optimal substrate for Sm antibodies.

EXAMPLE 6

In Vivo Ribozyme Catalyzed Cleavage of REV Pre-mRNA

The in vivo activity of the chimeric ribozymes was tested by coinjection of plasmid DNAs coding for the different U1-ribozymes and for the REV pre-mRNA into the nuclei of X. laevis oocytes. After overnight incubation the levels of accumulation of the different transcripts were analyzed by Northern blotting. The transcription of U1-ribozymes is driven by the homologous U1 snRNA gene promoter, while REV transcription is driven by the promoter of the X. laevis L14 ribosomal protein gene. The molar excess of U1 plasmid with respect to the REV plasmid (5:1) and the expected higher transcriptional activity of the U1 promoter, should ensure that U1-chimeric ribozymes are in excess over the REV transcripts. $^{32}$P-labelled U6 snRNA, known to be specifically retained inside the nucleus (20), was also coinjected. This RNA represents an internal control for successful nuclear injections of plasmid DNAs and for normalisation between different injections.

Figure 5:
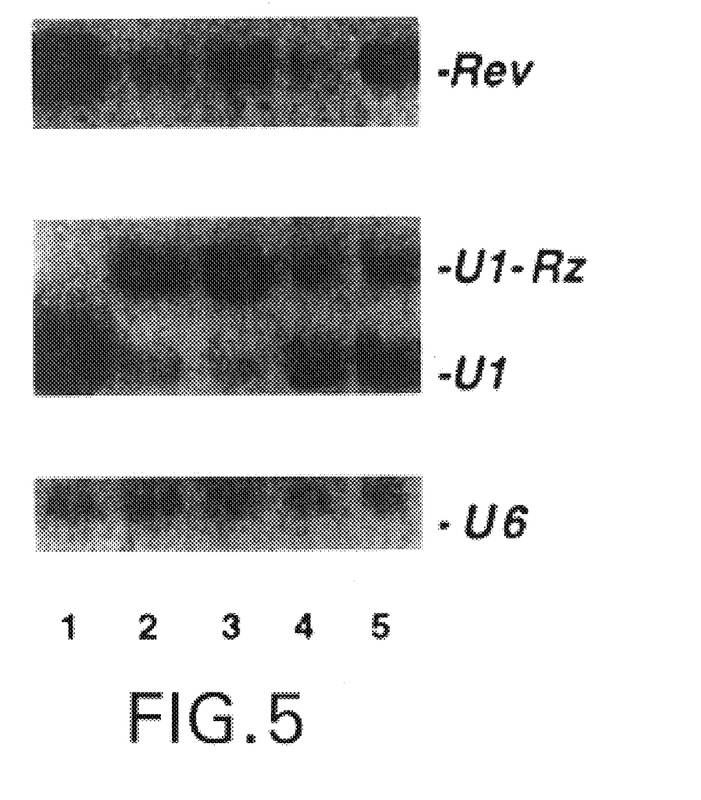

FIG. 5 shows a Northern blot analysis performed on RNA extracted from pools of 10 injected nuclei with either REV or U1 snRNA probes. Densitometric analysis of the gel has shown that the REV pre-mRNA signal is 15 times higher in injections where plasmid REV was coinjected with wild type U1-snRNA genes (lane 1) than with U1-Rz (lane 2). An additional twofold reduction is observed in injections of U1-Rz-5' (lane 4). The inactive versions of U1-ribozymes produce a destabilising effect on REV (lanes 3 and 5), very likely due to antisense activity (21). However the decrease is lower than the active ribozymes (half of the effect of the corresponding active form). These results show that the main activity responsible for the decreased accumulation of REV pre-mRNA is the catalytic cleavage produced by the active ribozymes. It is to be recalled that oocytes grow at 20° C., representing a non optimal temperature for the ribozyme activity.

The U6 signal in panel c derives from the injected $^{32}$P-labelled U6 snRNA and witnesses that the same amount of plasmid DNAs was correctly injected inside the nucleus.

As to human U1 snRNA chimeric molecules, U1h-ribozyme different constructs were cloned in the Bam H1 site of pSV2-neo plasmid and transfected in human CD4+ T-lymphocytes (Jurkat clone). Stable transformants were selected in G418 medium.

Single clones were amplified and the expression of different U1-ribozymes was tested by Northern blot analysis. Positive clones were selected and utilized for viral challenge with HIV-IIIB strain.

Figure 6:
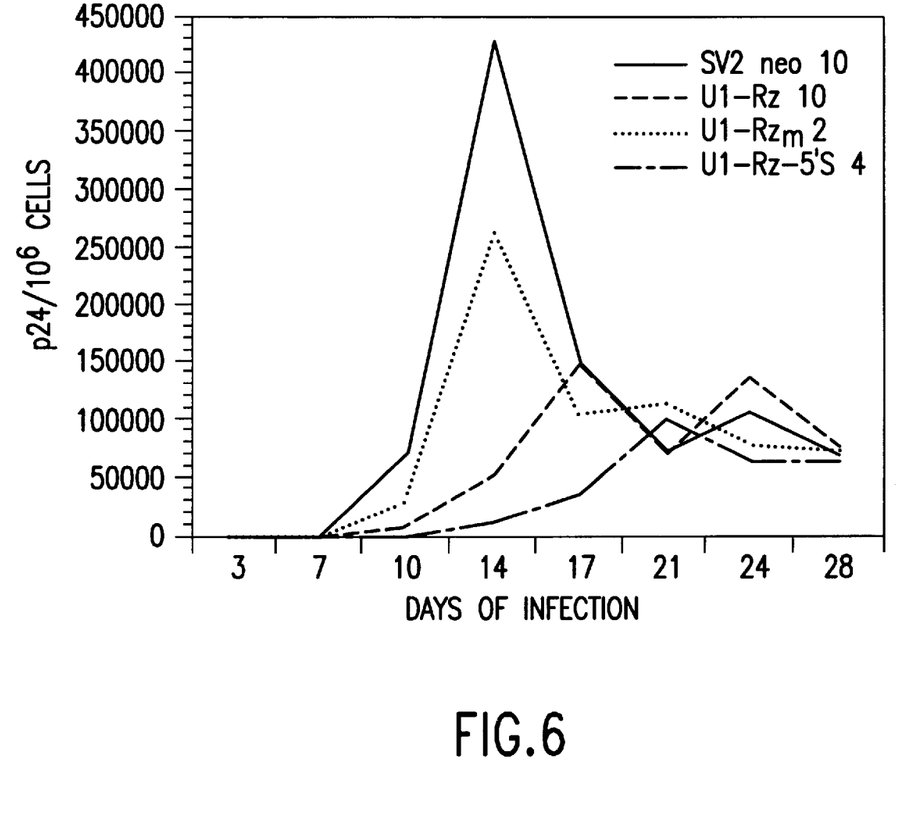
FIG. 6 shows a diagram showing the levels of HIV p24 protein released in the culture medium.

The progression of viral replication was followed by measuring, with immunological tests, the level of p24 capsid protein in the culture medium. FIG. 6 shows that in comparison to cells transfected with the control pSV2-neo plasmid alone, the active U1-Rz and U1-5'-Rz display protection activity against viral replication. In the case of U1-5'-Rz the effect reaches a 10-fold decrease in p24 levels. As control the disabled U1-Rz$_m$ display only little effect on p24 protein levels. Its partial activity can be attributed to the antisense effect mediated by the sequence complementarity with the substrate.

REFERENCES

1. Zaug, A. J., Been, M. D. and Cech, T. R. (1986) Nature 324, 429–433
2. Haseloff, J. and Gerlach W. L. (1988) Nature 334, 585–591
3. Symons, R. H. (1992) Annu Rev. Biochem. 61, 641–671
4. Sarver, N. and Rossi, J. J. (1993) J. NIH Res. 5, 63–67
5. Zhou, C., et al. (1994) Gene 149, 33–39
6. Yu, M., et al. (1995) Proc. Natl. Acad. Sci USA 92, 699–703
7. Reddy, R. and Bush, H. (1988). In "Structure and function of major and minor small nuclear ribonucleoprotein particles". Springer-Verlag, M. L. Birnstiel (ed.), pp. 1–37
8. Chang, D. D. and Sharp, P. A. (1989) Cell 59, 789–795
9. Stutz, F. and Rosbash, M. (1994) EMBO J. 13, 4096–4104
10. Fischer, U., et al. (1994) EMBO J. 13, 4105–4112
11. Uhlenbeck, O. C. (1987) Nature 328, 596–600
12. Ruffner, D. E., et al. (1990) Biochemistry 29, 10695–10702
13. Ratner, L., et al. (1984) Nature 313, 277–284
14. Zeller, R., et al. (1984) EMBO J. 3, 1075–1081
15. Traboni, C., et al. (1983) Nucleic Acids Res. 11, 4229–4239
16. Carnevali, F., et al. (1989) Nucleic Acids Res. 17, 8171–8184
17. Patton, J. R., et al. (1989) Mol. Cell. Biol. 9, 3360–3368
18. Terns, M. P., Lund, E. and Dahlberg, J. E. (1993) Nucleic Acids Res. 21, 4569–4573
19. Caffarelli E., et al. (1987) EMBO J. 6: 3493–3498
20. Terns, M. P. and Dahlberg, J. E. (1994) Science 264, 959–961
21. Dropulic, et al. (1993) Antisense Research and Development 3, 87–94

I claim:

1. A chimeric ribozyme molecule comprising:
    (a) a U1 snRNA vector component which targets the chimeric ribozyme molecule to a substrate target RNA in the spliceosome of a cell nucleus; and
    (b) a ribozyme-derived component having a catalytic endonuclease activity toward the substrate target RNA, wherein the vector component is covalently linked to the ribozyme-derived component.

2. The chimeric ribozyme molecule of claim 1 wherein the snRNA is from an organism selected from the group consisting of *Xenopus laevis,* humans and non-human mammals.

3. The chimeric ribozyme molecule of claim 1 wherein a portion of the nucleotide sequence of said U1 snRNA is substituted with the nucleotide sequence of a ribozyme having a catalytic endonuclease activity towards the target substrate RNA, wherein said substitution does not substantially impair U1 snRNA targeting of the chimeric molecule to the substrate target RNA in the spliceosome of the cell nucleus.

4. The chimeric ribozyme molecule of claim 3 wherein said substituted portion of the U1 snRNA is the portion forming the stem-loop III structure of U1 snRNA.

5. A chimeric ribozyme molecule comprising:
    (a) a U1 snRNA vector component which targets the chimeric ribozyme molecule to a substrate target RNA in the spliceosome of a cell nucleus which is selected from the group consisting of an altered form of a cellular RNA and a viral RNA; and
    (b) a ribozyme-derived component having a catalytic endonuclease activity toward the substrate target RNA, wherein the vector component is covalently linked to the ribozyme-derived component.

6. The chimeric ribozyme molecule according to claim 5 wherein the substrate target RNA is a human immunodeficiency virus RNA.

7. The chimeric ribozyme molecule according to claim 6 wherein the human immunodeficiency virus RNA is the REV pre-mRNA.

8. The chimeric ribozyme molecule according to claim 7 wherein the sequence of the ribozyme-derived component of said chimeric ribozyme molecule is either identical or substantially homologous to the sequence of SEQ ID NO:1 wherein the substantially homologous sequence maintains catalytic endonuclease activity toward a substrate target RNA.

9. A chimeric ribozyme molecule comprising:
    (a) a U1 snRNA vector component which targets the chimeric ribozyme molecule to a substrate target RNA, wherein the U1 snRNA-derived vector component is modified to increase its affinity for the target substrate RNA; and
    (b) a ribozyme-derived component having a catalytic endonuclease activity toward the substrate target RNA, wherein the vector component is covalently linked to the ribozyme-derived component.

10. The chimeric ribozyme molecule of claim 9 wherein the snRNA-derived vector component is modified by means of one or more nucleotide substitutions of the sequence recognizing the 5' splice site of the target substrate RNA.

11. The chimeric ribozyme molecule according to claim 1 wherein the sequence of the vector component of said chimeric molecule is either identical or substantially homologous to the sequence of SEQ ID NO:2, wherein the substantially homologous sequence targets the chimeric ribozyme molecule to a target substrate RNA in the spliceosome of a cell nucleus and the ribozyme-derived component maintains catalytic endonuclease activity toward the substrate target RNA.

12. A nucleic acid encoding the chimeric ribozyme molecule of claim 1, 5, 8, 9 or 11.

13. A nucleic acid encoding the chimeric ribozyme molecule of claim 1 and having a sequence comprised in SEQ ID NO:3 or a complementary strand thereof.

\* \* \* \* \*

UNITED STATES PATENT AND TRADEMARK OFFICE
CERTIFICATE OF CORRECTION

PATENT NO. : 5,994,124  
DATED : November 30, 1999  
INVENTOR(S) : Irene Bozzoni Page 1 of 1

It is certified that error appears in the above-identified patent and that said Letters Patent is hereby corrected as shown below:

<u>Title page,</u>  
Item [56], References Cited, OTHER PUBLICATIONS,  
Under "Functional...etc.", "Intracellular," should read -- Intracellular --;  
Under "Orkin et al", "et al" should read -- et al. --;  
Under "Tani, T. et al", "et al" should read -- et al. --;  
Under "Michienzi et al", "et al" should read -- et al. --; "(-)STRSV" should read -- (-)sTRSV --;

<u>Column 6,</u>  
Line 19, "5'-GAU<u>ACUUACU</u>GGGC-3" should read  
-- 5'-GAU<u>ACUUACU</u>GGGC-3 --.

Signed and Sealed this

Twelfth Day of February, 2002

Attest:

JAMES E. ROGAN  
Attesting Officer  Director of the United States Patent and Trademark Office

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
       (A) LENGTH: 38 base pairs
       (B) TYPE: nucleic acid
       (C) STRANDEDNESS: single
       (D) TOPOLOGY: linear (xi) SEQUENCE DESCRIPTION: SEQ ID NO: 1:

AUGAGUCUCU GAUGAGUCCG UGAGGACGAA ACUGCCUU                                     38

(2) INFORMATION FOR SEQ ID NO: 2:

(i) SEQUENCE CHARACTERISTICS:
       (A) LENGTH: 179 base pairs
       (B) TYPE: nucleic acid
       (C) STRANDEDNESS: single
       (D) TOPOLOGY: linear (xi) SEQUENCE DESCRIPTION: SEQ ID NO: 2:

AUACUUACCU GGCAGGGGAG AUACCAUGAU CACGAAGGUG GUUUUCCCAG GGCGAGGCUU      60

AUCCAUUGCA CUCCGGAUGU GCUGACCCCU GCGAUGAGUC UCUGAUGAGU CCGUGAGGAC     120

GAAACUGCCU UCGACUGCAU AAUUUGUGGU AGUGGGGAC UGCGUUCGCG CUUUCCCCU      179

(2) INFORMATION FOR SEQ ID NO: 3:

(i) SEQUENCE CHARACTERISTICS:
       (A) LENGTH: 435 base pairs
       (B) TYPE: nucleic acid
       (C) STRANDEDNESS: double
       (D) TOPOLOGY: linear (xi) SEQUENCE DESCRIPTION: SEQ ID NO: 3:

AGGGCGACTT CTATGTAGAT GAGGCAGCGC AGAGGCTGCC TTGTTCGCCA CTTGCTGCTT      60

CACCACGAAG GAGTTCCCGT GCCCTGGGAG CGGGTTCAGG ACCGCTGATC GGAAGTGAGA    120

ATCCCAGCTG TGTGTCAGGG CTGGAAAGGG CTCGGGAGTG CGCGGGGCAA GTGACCGTGT    180

GTGTAAAGAG TGAGGGTATG AGGCTGTGTC GGGGCAGAGG CCCAAGATCT CATACTTACC    240

```
TGGCAGGGGA GATACCATGA TCACGAAGGT GGTTTTCCCA GGGCGAGGCT TATCCATTGC      300

ACTCCGGATG TGCTGACCCC TGCGATGAGT CTCTGATGAG TCCGTGAGGA CGAAACTGCC      360

TTCGACTGCA TAATTTGTGG TAGTGGGGGA CTGCGTTCGC GCTTTCCCCT GACTTTCTGG      420

AGTTTCAAAA GTAGA                                                       435
```

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (xi) SEQUENCE DESCRIPTION: SEQ ID NO: 4:

```
UCAAGGCAGU CAGACUCAUC A                                                 21
```

(2) INFORMATION FOR SEQ ID NO: 5:

(i) SEQUENCE CHARACTERISTICS:
        (A) LENGTH: 43 base pairs
        (B) TYPE: nucleic acid
        (C) STRANDEDNESS: single
        (D) TOPOLOGY: linear     (xi) SEQUENCE DESCRIPTION: SEQ ID NO: 5:

```
GGACTCATCA SAGACTCATC ACGCAGGGGT CAGCACAACC GGA                         43
```

(2) INFORMATION FOR SEQ ID NO: 6:

(i) SEQUENCE CHARACTERISTICS:
        (A) LENGTH: 43 base pairs
        (B) TYPE: nucleic acid
        (C) STRANDEDNESS: single
        (D) TOPOLOGY: linear     (xi) SEQUENCE DESCRIPTION: SEQ ID NO: 6:

```
GTGAGGACGA AACTGCCTTG ACGACTGCAT AATTTCTGGT AGT                         43
```

(2) INFORMATION FOR SEQ ID NO: 7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (xi) SEQUENCE DESCRIPTION: SEQ ID NO: 7:

```
TGGGCAGGGG AGATACCATG                                                   20
```

(2) INFORMATION FOR SEQ ID NO: 8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (xi) SEQUENCE DESCRIPTION: SEQ ID NO: 8:

```
GTAAGTATGA GTTGAACAAG                                                   20
```

(2) INFORMATION FOR SEQ ID NO: 9:

(i) SEQUENCE CHARACTERISTICS:
        (A) LENGTH: 41 base pairs
        (B) TYPE: nucleic acid (C) STRANDEDNESS: single
        (D) TOPOLOGY: linear (xi) SEQUENCE DESCRIPTION: SEQ ID NO: 9:

GGACTCATCA GAGACTCATG AGAATCATAC CACTAGACCA T                              41

(2) INFORMATION FOR SEQ ID NO: 10:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 10:

GTGAGGACGA AACTGCCTTT GGGTGCGAGA GGTCCCGGGT T                              41

(2) INFORMATION FOR SEQ ID NO: 11:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 11:

GAUACUUACC UGGC                                                            14

(2) INFORMATION FOR SEQ ID NO: 12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 12:

GAUACUUACU GGGC                                                            14

(2) INFORMATION FOR SEQ ID NO: 13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 13:

CCGGATCCTA AGGACCAGCT TCTTTGGG                                             28

(2) INFORMATION FOR SEQ ID NO: 14:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 14:

CCGGATCCTT AGCGTACAGT CTACTTTT                                             28

(2) INFORMATION FOR SEQ ID NO: 15:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO: 15:

GGACTCATCA SAGACTCATC GCAGGGGTCA GCACATCCGG A                              41

(2) INFORMATION FOR SEQ ID NO: 16:

(i) SEQUENCE CHARACTERISTICS:
            (A) LENGTH: 41 base pairs
            (B) TYPE: nucleic acid
            (C) STRANDEDNESS: single
            (D) TOPOLOGY: linear (xi) SEQUENCE DESCRIPTION: SEQ ID NO: 16:

GTGAGGACGA AACTGCCTTC GACTGCATAA TTTGTGGTAG T                              41

(2) INFORMATION FOR SEQ ID NO: 17:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 17:

TGGGCAGGGG AGATACCATG                                                      20

(2) INFORMATION FOR SEQ ID NO: 18:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (xi) SEQUENCE DESCRIPTION: SEQ ID NO: 18:

GTAAGTATGA GATCTTGGGC                                                      20

(2) INFORMATION FOR SEQ ID NO:19:

(i) SEQUENCE CHARACTERISTICS:
            (A) LENGTH: 42 bases
            (B) TYPE: nucleic acid
            (C) STRANDEDNESS: single
            (D) TOPOLOGY: linear (xi) SEQUENCE DESCRIPTION: SEQ ID NO:19:

UGAUGAGUCU CUGAUGAGUC CGUGAGGACG AAACUGCCUU GA                             42

(2) INFORMATION FOR SEQ ID NO:20:

(i) SEQUENCE CHARACTERISTICS:
            (A) LENGTH: 14 bases
            (B) TYPE: nucleic acid
            (C) STRANDEDNESS: single
            (D) TOPOLOGY:linear (xi) SEQUENCE DESCRIPTION:SEQ ID NO:20:

CGGUCCAUUC AUAG                                                            14

(2) INFORMATION FOR SEQ ID NO:21:

(i) SEQUENCE CHARACTERISTICS:
            (A) LENGTH: 14 bases
            (B) TYPE: nucleic acid
            (C) STRANDEDNESS: single
            (D) TOPOLOGY: linear (xi) SEQUENCE DESCRIPTION: SEQ ID NO:21:

```
CGGGUCAUUC  AUAG                                                              14
```

(2) INFORMATION FOR SEQ ID NO:22:

(i) SEQUENCE CHARACTERISTICS:
        (A) LENGTH: 434 bases
        (B) TYPE: nucleic acid
        (C) STRANDEDNESS: single
        (D) TOPOLOGY: linear     (xi) SEQUENCE DESCRIPTION: SEQ ID NO:22:

```
AGGGCGACTT CTATGTAGAT GAGGCAGCGC AGAGGCTGCC TTGTCGCCAC TTGCTGCTTC      60

ACCACGAAGG AGTTCCCGTG CCCTGGGAGC GGGTTCAGGA CCGCTGATCG GAAGTGAGAA     120

TCCCAGCTGT GTGTCAGGGC TGGAAGGGCT CGGGAGTGCG CGGGGCAAGT GACCGTGTGT     180

GTAAAGAGTG AGGCGTATGA GGCTGTGTCG GGGCAGAGGC CCAAGATCTC ATACTTACTG     240

GGCAGGGGAG ATACCATGAT CACGAAGGTG GTTTTCCCAG GGCGAGGCTT ATCCATTGCA     300

CTCCGGATGT GCTGACCCCT GCGATGAGTC TCTGATGAGT CCGTGAGGAC GAAACTGCCT     360

TCGACTGCAT AATTTGTGGT AGTGGGGGAC TGCGTTCGCG CTTTCCCCTG ACTTTCTGGA     420

GTTTCAAAAG TAGA                                                      434
```